US012763212B2

(12) United States Patent
Petricoin, III et al.

(10) Patent No.: US 12,763,212 B2
(45) Date of Patent: Oct. 13, 2026

(54) METHODS FOR PREDICTING RELATIVE BENEFIT OF THERAPY OPTIONS AND DEVICES THEREOF

(71) Applicant: Perthera, Inc., McLean, VA (US)

(72) Inventors: Emanuel Frank Petricoin, III, Gainsville, VA (US); Edik Matthew Blais, Charlottesville, VA (US); Hieu Trung Nguyen, Jackson Heights, NY (US)

(73) Assignee: Perthera, Inc., McLean, VA (US)

( * ) Notice: Subject to any disclaimer, the term of this patent is extended or adjusted under 35 U.S.C. 154(b) by 82 days.

(21) Appl. No.: 18/731,179

(22) Filed: May 31, 2024

(65) Prior Publication Data

US 2024/0404705 A1 Dec. 5, 2024

Related U.S. Application Data

(60) Provisional application No. 63/505,217, filed on May 31, 2023.

(51) Int. Cl.
*G16H 50/20* (2018.01)
*G16H 50/70* (2018.01)

(52) U.S. Cl.
CPC ............. *G16H 50/20* (2018.01); *G16H 50/70* (2018.01)

(58) Field of Classification Search
None
See application file for complete search history.

(56) References Cited

U.S. PATENT DOCUMENTS

| | | | | |
|---|---|---|---|---|
| 11,538,583 | B2 * | 12/2022 | Isobe | G16H 10/60 |
| 12,357,240 | B2 * | 7/2025 | Ekström | G16H 50/50 |
| 12,586,685 | B2 * | 3/2026 | Vladimirova | G16H 50/20 |
| 2011/0238321 | A1 * | 9/2011 | Slotman | G01N 33/564 702/19 |
| 2014/0058683 | A1 * | 2/2014 | Slotman | G16H 10/20 702/19 |
| 2015/0376710 | A1 * | 12/2015 | Hatzis | G16B 20/00 702/20 |
| 2017/0116379 | A1 * | 4/2017 | Scott | G16H 50/20 |
| 2017/0276676 | A1 * | 9/2017 | Slotman | G16H 20/10 |
| 2019/0355478 | A1 * | 11/2019 | Madhavan | A61N 5/103 |

(Continued)

*Primary Examiner* — Jonathan Ng
(74) *Attorney, Agent, or Firm* — Troutman Pepper Locke LLP

(57) ABSTRACT

Methods, non-transitory computer-readable media, and devices are disclosed that identify and validate a signature for predicting relative benefit of two therapies for frontline and therapy sequencing for patients. Described and illustrated by way of the example herein are machine learning approaches for gaining data-driven insights from the mutational landscape in metastatic pancreatic adenocarcinoma (mPDAC) and validating the signature in predicting relative benefit from FOLFIRINOX (FFX) and Gemcitabine/nab-Paclitaxel (GA) therapies. This technology inputs a patient's genomics findings and clinical data and generates predictions of relative effectiveness for the two distinct FFA and GA chemotherapy options. The predictions for an individual patient provide personalized guidance on treatment sequencing to improve patient health outcomes.

5 Claims, 14 Drawing Sheets
(11 of 14 Drawing Sheet(s) Filed in Color)

(56) References Cited

U.S. PATENT DOCUMENTS

| | | | | |
|---|---|---|---|---|
| 2019/0385740 | A1* | 12/2019 | Madhavan | G16H 50/50 |
| 2020/0219592 | A1* | 7/2020 | Gruber | G16H 50/20 |
| 2021/0057071 | A1* | 2/2021 | Barber | G16H 10/60 |
| 2021/0327540 | A1* | 10/2021 | Schobel | G06N 20/20 |
| 2022/0108262 | A1* | 4/2022 | Cella | G06Q 10/063118 |
| 2022/0319658 | A1 | 10/2022 | Abraham et al. | |
| 2023/0047712 | A1* | 2/2023 | Curtis | G16B 25/10 |
| 2023/0049979 | A1* | 2/2023 | Issler | G16B 25/00 |
| 2024/0006080 | A1* | 1/2024 | Molero Leon | G16H 10/60 |
| 2024/0076368 | A1* | 3/2024 | Akmaev | G16B 40/20 |
| 2024/0105303 | A1* | 3/2024 | Auslander | G16H 20/10 |
| 2024/0274286 | A1* | 8/2024 | Chen | G16H 50/70 |
| 2024/0321465 | A1* | 9/2024 | Eckhoff | G16H 20/10 |
| 2024/0420848 | A1* | 12/2024 | Sams | G16H 10/60 |
| 2025/0022609 | A1* | 1/2025 | Garcia-Alcalde | G16H 20/10 |
| 2025/0111917 | A1* | 4/2025 | Toki | G16H 50/20 |
| 2025/0157665 | A1* | 5/2025 | Ahmed | G16B 20/00 |
| 2025/0259724 | A1* | 8/2025 | Crabtree | G16H 50/50 |

* cited by examiner

METHODS FOR PREDICTING RELATIVE BENEFIT OF THERAPY OPTIONS AND DEVICES THEREOF

This application claims priority to U.S. Provisional Patent Application No. 63/505,217, filed May 31, 2023, which is hereby incorporated by reference herein in its entirety.

FIELD

This technology generally relates to machine learning methods and devices for evaluating patient treatment options and generating treatment recommendations and, more particularly, to methods and device for predicting relative benefit of therapy options (e.g., for patients with metastatic pancreatic cancer).

BACKGROUND

Pancreatic adenocarcinoma (PDAC) is an aggressive disease with poor clinical outcomes. The two most prescribed standard combinations of chemotherapy in PDAC according to NCCN and ASCO guidelines are FFX and GA. FFX refers to the combination commonly abbreviated as FOLFIRINOX which includes three distinct types of chemotherapeutic agents: (1) 5-Fluorouracil (commonly abbreviated as 5FU) represents the backbone of this regimen; (2) Irinotecan is a secondary agent commonly used in combination with 5FU (+/−oxaliplatin); and (3) Oxaliplatin is a secondary agent commonly used in combination with 5FU (+/−irinotecan). Alternatives for Irinotecan in the same class are nanoliposomal irinotecan (nal-irinotecan) and topotecan and alternatives for Oxaliplatin in the same class are cisplatin and carboplatin.

GA refers to the combination commonly abbreviated as Gemcitabine/Abraxane or Gem/nab-P and includes two distinct types of chemotherapeutic agents: (1) Gemcitabine represents the backbone of this regimen and (2) nab-Paclitaxel is a secondary agent commonly used in combination with gemcitabine. Alternatives for nab-Paclitaxel in the same class are paclitaxel and docetaxel.

FFX and GA are both commonly given to patients with PDAC as the first line of therapy for treating advanced or metastatic disease but not typically simultaneously. Patients who receive a 1st line or frontline therapy consisting of FFX usually receive GA as their 2nd line of therapy. Conversely, patients who receive 1st line GA usually receive a variation of FFX as their 2nd line of therapy (more specifically, 5FU+nal-irinotecan according to standard guidelines). Currently, the clinical decision to recommend 1st line FFX over 1st line GA (or vice versa) by an oncology care team depends on a multitude of factors regarding an individual patient's past medical and treatment history, the patient's performance status, the patient's age at the time of cancer diagnosis (or time of the treatment decision), and the presence/absence of a genomic alteration in either BRCA1, BRCA2, or PALB2 based on germline testing of those genes or genomic sequencing of the tumor via tumor biopsy or liquid biopsy.

However, nearly half of patients with PDAC never receive a 2nd line of therapy for metastatic PDAC (mPDAC) following frontline FFX or GA therapy. While genomic alterations in the DDR pathway (e.g., BRCA 1/2) are associated with increased progression-free survival (PFS) on platinum-containing regimens (e.g., FFX), other biomarkers that predict benefit from GA and/or FFX in PDAC are currently unexplored and/or unknown. Unfortunately, current clinical PDAC treatment recommendations are insufficiently informed, and the resulting treatments and/or therapy sequencing lack sufficient efficacy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

This technology generally relates to identifying and validating a signature for predicting relative benefit from frontline FOLFIRINOX (FFX) and Gemcitabine/nab-Paclitaxel (GA) for patients with metastatic pancreatic cancer (mPDAC). Described and illustrated by way of the example herein are machine learning approaches for gaining data-driven insights from the mutational landscape in mPDAC and validating the signature in predicting relative benefit from FFX and GA. More specifically, this technology inputs a patient's genomics findings and clinical data and generates predictions of relative effectiveness for the two distinct FFA and GA standard chemotherapy options. The predictions for an individual patient provide personalized guidance on treatment sequencing with the two most prescribed standard combinations of chemotherapy in PDAC according to NCCN and ASCO guidelines. While the technology described and illustrated herein is explained with reference to an exemplary context of mPDAC and FFX and GA treatment options, this technology can be used to train, deploy, and apply machine learning models configured to generate personalized predictive outputs for any number of other therapy options for other conditions (e.g., Non-Small Cell Lung Cancer (NSCLC) chemotherapy or immunotherapy).

Figure 1:
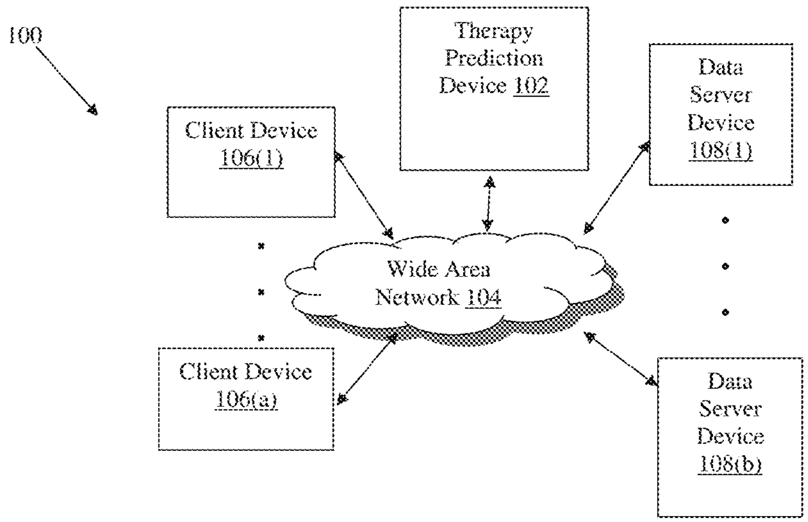
FIG. 1 is a block diagram of an exemplary network environment that includes a therapy prediction device.

Referring now to FIG. 1, an exemplary network environment 100 is illustrated that includes a therapy prediction device 102 coupled, via a wide area network (WAN) 104, to client devices 106(1)-106(*a*) and data server devices 108(1)-108(*b*). The network environment 100 may include other network devices such as one or more routers or switches, for example, which are known in the art and thus will not be described herein. This technology provides a number of advantages including methods, non-transitory computer readable media, and therapy prediction devices that more effectively predict relative benefit of therapy options for patients with mPDAC to provide a recommended treatment plan with increased efficacy.

In this example, the client devices 106(1)-106(*a*), therapy prediction device 102, and data server devices 108(1)-108(*b*) are disclosed in FIG. 1 as dedicated hardware devices. However, one or more of the client devices 106(1)-106(*a*), therapy prediction device 102, or data server devices 108(1)-108(*n*) can also be implemented in software within one or more other devices in the network environment 100. As one example, the therapy prediction device 102, as well as any of its components or applications, can be implemented as software executing on one of the data server devices 108(1)-108(*b*), and many other permutations and types of implementations and network topologies can also be used in other examples.

Figure 2:
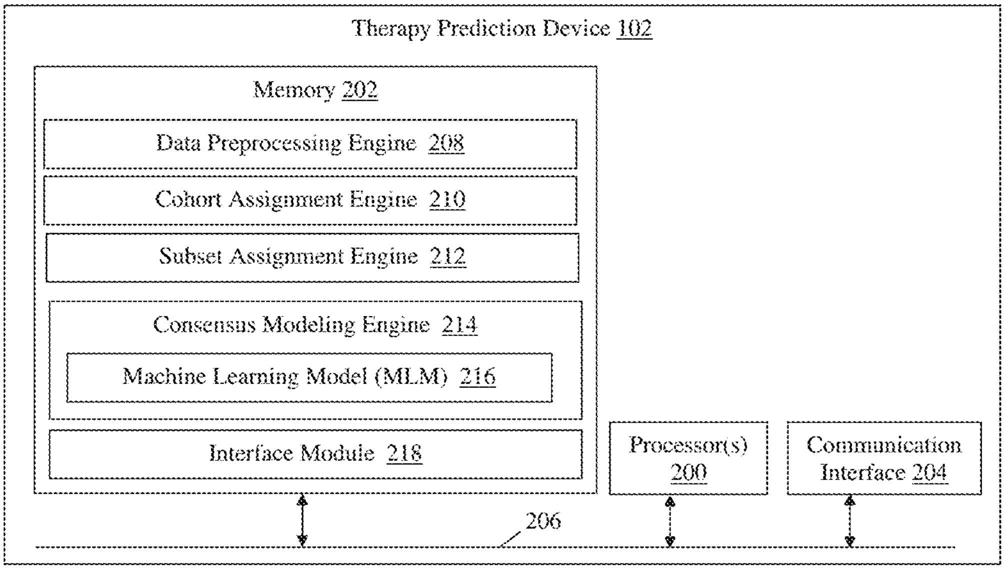
FIG. 2 is a block diagram of an exemplary therapy prediction device.

Referring to FIGS. 1-2, the therapy prediction device 102 of the network environment 100 may perform any number of functions, including training and validating machine learning models and providing interfaces to the client devices 106(1)-106(*a*) for ingesting patient-specific data and receiving instructions. The therapy prediction device 102 in this example includes processor(s) 200, a memory 202, and a communication interface 204, which are coupled together by a bus 206, although the therapy prediction device 102 can include other types or numbers of elements in other configurations.

The processor(s) 200 of the therapy prediction device 102 may execute programmed instructions stored in the memory 202 of the therapy prediction device 102 for any number of the functions described and illustrated herein. The processor(s) 200 may include one or more central or graphics processing units and/or one or more processing cores, for example, although other types of processor(s) can also be used.

The memory 202 of the therapy prediction device 102 stores these programmed instructions for one or more aspects of the present technology as described and illustrated herein, although some or all the programmed instructions could be stored elsewhere. A variety of different types of memory storage devices, such as random-access memory (RAM), read only memory (ROM), hard disk, solid state drives, flash memory, or other computer readable medium which is read from and written to by a magnetic, optical, or other reading and writing system that is coupled to the processor(s) 200, can be used for the memory 202.

Accordingly, the memory 202 can store applications that can include computer executable instructions that, when executed by the therapy prediction device 102, cause the therapy prediction device 102 to perform actions, such as to transmit, receive, or otherwise process network messages and requests, for example, and to perform other actions described and illustrated below. The application(s) can be implemented as components of other applications, operating system extensions, and/or plugins, for example.

Further, the application(s) may be operative in a cloud-based computing environment with access provided via a software-as-a-service (SaaS) model. The application(s) can be executed within or as virtual machine(s) or virtual server(s) that may be managed in a cloud-based computing environment. Also, the application(s), and even the therapy prediction device 102 itself, may be in virtual server(s) running in a cloud-based computing environment rather than being tied to specific physical network computing devices. Also, the application(s) may be running in virtual machines (VMs) executing on the therapy prediction device 102 and managed or supervised by a hypervisor.

In this example, the memory 202 includes a data preprocessing engine 208, a cohort assignment engine 210, a subset assignment engine 212, a consensus modeling engine 214 with a machine learning model (MLM) 216, and an interface module 218, although applications, engines, or modules also can be hosted by the therapy prediction device 102 in other examples. The data preprocessing engine 208 is generally configured to obtain input data including molecular data, clinical data, and outcome data for a historical set of patients from one or more of the data server devices 108(1)-108(*b*). The input data or a portion thereof is then preprocessed to convert raw or unstructured data to a structured format useful for training and validating the MLM 216.

The cohort assignment engine 210 is generally configured to assign patients corresponding to portions (e.g., rows) of the input data to independent training and validation cohorts that can be used to train and validate the MLM 216, respectively. The cohort assignment engine 210 can establish the training and validation cohorts to minimize potential bias of potential or known confounders to ensure balanced representation of important features, as described and illustrated in more detail below.

The subset assignment engine 212 in some examples is generally configured to select the patients and/or features from the training cohort that are to be inputs for training a single model of a plurality of models that can collectively form the ensemble MLM 216. Thus, the single models may vary based on the chosen sampling method for the patients and/or features, as also explained in more detail below.

The consensus modeling engine 214 is generally configured to use the training and validation cohorts and output of the subset assignment engine to train and cross-validate the MLM 216. The MLM in this example is generally trained to analyze patient data and provide treatment plans or sequencing with recommended therapies, as described and illustrated in more detail below.

The interface module 218 is configured to provide graphical user interfaces (GUIs) for receiving patient data to be applied to the MLM 216 and/or for outputting graphical representations of recommended treatment options with associated response probabilities. The interface module 218 can also provide application programming interfaces (APIs) accessible to third parties (e.g., clinical professionals or insurance companies) for obtaining patient data and providing a report including output of the MLM 216 in the form of recommended therapies, for example.

The communication interface 204 of the therapy prediction device operatively couples and communicates between the therapy prediction device 102, client devices 106(1)-106(*a*), and data server devices 108(1)-108(*b*), which are coupled together at least in part by the WAN 104, although other types or numbers of communication networks or systems with other types or numbers of connections or configurations to other devices or elements can also be used.

While a WAN 104 is disclosed in this example, the WAN 104 can include any type of communication network(s) including local area network(s) (LAN(s)) and can use TCP/IP over Ethernet and industry-standard protocols, although other types or numbers of protocols or communication networks can be used. The WAN 104 in this example can employ any suitable interface mechanisms and network communication technologies including, for example, Ethernet-based Packet Data Networks (PDNs).

While the therapy prediction device 102 is illustrated in this example as including a single device, the therapy prediction device 102 in other examples can include a plurality of devices each having one or more processors (each processor with one or more processing cores) that implement one or more steps of this technology (e.g., one device for training and deploying the MLM216 and another device for hosting and applying the deployed MLM 216 to obtained patient data). In these examples, one or more of the devices can have a dedicated communication interface or memory. Alternatively, one or more of the devices can utilize the memory, communication interface, or other hardware or software components of one or more other devices included in the therapy prediction device 102. Additionally, one or more of the devices that together comprise the therapy prediction device 102 in other examples can be standalone devices or integrated with one or more other devices or apparatuses.

Each of the client devices 106(1)-106(*a*) of the network environment 100 in this example includes any type of computing device that can exchange network data, such as mobile, desktop, laptop, or tablet computing devices, virtual machines (including cloud-based computers), or the like. Each of the client devices 106(1)-106(*a*) in this example includes a processor, a memory, and a communication interface, which are coupled together by a bus or other communication link (not illustrated), although other numbers or types of components could also be used.

Each of the client devices 106(1)-106(*a*) may run interface applications, such as standard web browsers or the standalone applications, which may provide an interface to communicate with the therapy prediction device 102 via the WAN 104. Each of the client devices 106(1)-106(*a*) may further include a display device, such as a display screen or touchscreen, or an input device, such as a keyboard or mouse, for example (not illustrated).

Each of the data server devices 108(1)-108(*b*) in this example includes one or more processors, a memory, and a communication interface, which are coupled together by a bus or other communication link, although other numbers and types of network devices could be used. The data server devices 108(1)-108(*b*) in this example host historical molecular and/or clinical data for a plurality of patients and/or patient data for particular patients for which a treatment plan is sought. The data server devices 108(1)-108(*b*) may be hardware or software or may represent a system with multiple servers or other devices in a pool, which may include internal or external networks.

Although the data server devices 108(1)-108(*b*) are illustrated as single devices, one or more actions of each of the data server devices 108(1)-108(*b*) may be distributed across one or more distinct network computing devices that together comprise one or more of the data server devices 108(1)-108(*b*). Moreover, the data server devices 108(1)-108(*b*) are not limited to a particular configuration. Thus, the data server devices 108(1)-108(*b*) may contain a plurality of network computing devices that operate using a master/slave approach, whereby one of the network computing devices of the data server devices 108(1)-108(*b*) operate to manage and/or otherwise coordinate operations of the other network computing devices. The data server devices 108(1)-108(*b*) may operate as a plurality of network computing devices within a cluster architecture, a peer-to peer architecture, virtual machines, or within a cloud or any other type of decentralized architecture or topology, for example.

Although the exemplary network environment 100 with the client devices 106(1)-106(*a*), therapy prediction device 102, data server devices 108(1)-108(*n*), and WAN 104 are described and illustrated herein, other types or numbers of systems, devices, components, or elements in other topologies can be used. It is to be understood that the systems of the examples described herein are for exemplary purposes, as many variations of the specific hardware and software used to implement the examples are possible, as will be appreciated by those skilled in the relevant art(s).

One or more of the components depicted in the network environment 100, such as the client devices 106(1)-106(*a*), therapy prediction device 102, or data server devices 108 (1)-108(*b*), for example, may be configured to operate as virtual instances on the same physical machine. In other words, one or more of the client devices 106(1)-106(*a*), therapy prediction device 102, or data server devices 108 (1)-108(*b*) may operate on the same physical device rather than as separate devices communicating through the WAN 104 and/or the decentralized network. Additionally, there may be more or fewer client devices, therapy prediction devices, or data server devices than illustrated in FIG. 1.

The examples of this technology may also be embodied as one or more non-transitory computer readable media having instructions stored thereon, such as in the memory 202 of the therapy prediction device 102, for one or more aspects of the present technology, as described and illustrated by way of the examples herein. The instructions in some examples include executable code that, when executed by one or more processors, such as the processor(s) 200 of the therapy prediction device 102, cause the processors to carry out steps necessary to implement the methods of the examples of this technology that will now be described and illustrated herein.

Figure 3:
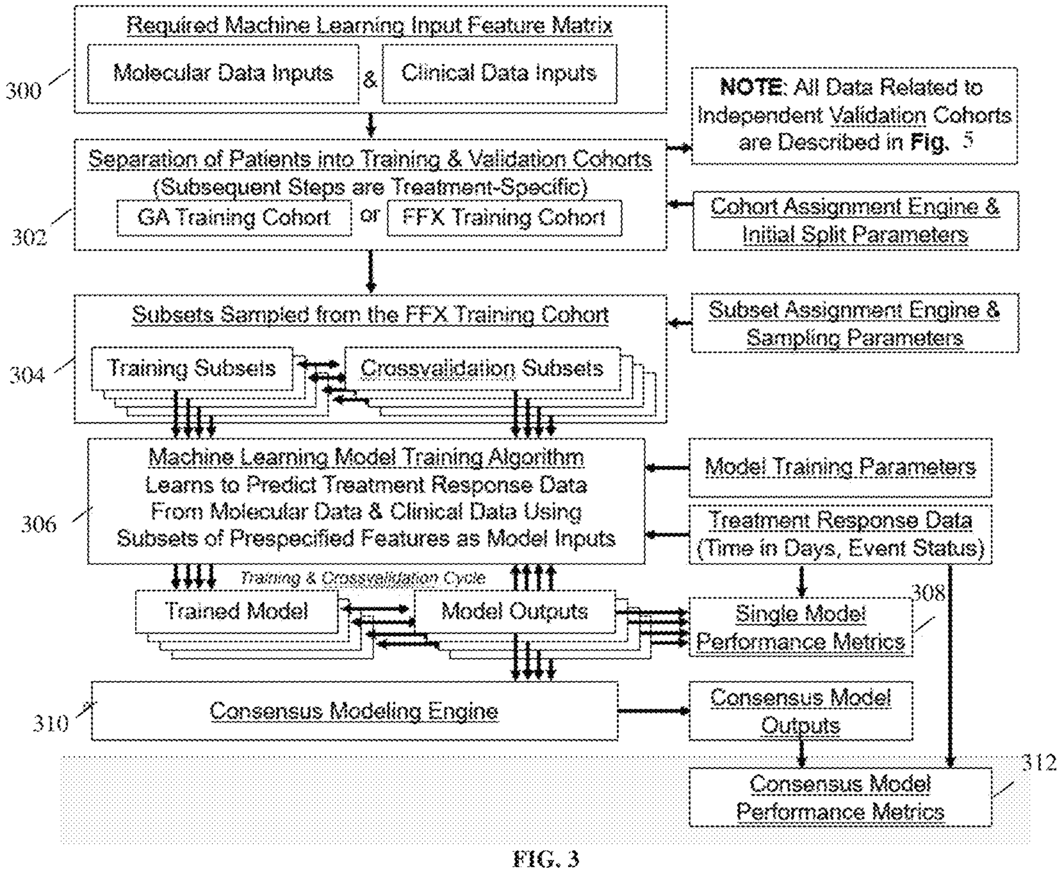
FIG. 3 is a flowchart of an exemplary method for training treatment-specific models.

Referring now to FIG. 3, a flowchart of an exemplary method for training treatment-specific models (e.g., the MLM 216) is illustrated. In step 300 in this example, the therapy prediction device 102 obtains training and validation data including molecular data and clinical data for a plurality of patients, which is also referred to herein as a machine learning input feature matrix. The training and validation data can be obtained from third party databases hosted by the data server devices 108(1)-108(*b*), for example. In some examples, the training and validation data includes clinical data such as patient sex, patient age at diagnosis (e.g., younger or older than 63), cancer stage details, and/or other or demographic, personal, or clinical data. The molecular data of the training and validation data can include next generation sequencing (NGS) data, immunohistochemistry (IHC) data, ribonucleic acid (RNA) data, and/or other molecular data for each patient.

In some examples, the training and validation data includes variant-level clusters of genomic features (1 if a clinically significant variant as described is present), gene-level clusters of genomic features (1 if a clinically significant result is present), pathway-level clusters of genomic features (1 if clinically significant result is present in any gene by type as listed), and/or network-level clusters of genomic features (1 if any clinically significant result for pathways or genes), although other types of training and validation data can also be used in other examples. In some examples, the variant-level clusters of genomic features can include KRAS G12D, KRAS G12V, KRAS G12R, KRAS G12C, KRAS Q61 (any affecting this codon), and/or KRAS A146/K117/etc. (any significant atypical KRAS variant not described above). The gene-level clusters of genomic features can include:

KRAS Mutation (any significant short variant)
TP53 Alteration (any significant short variant or structural variant or copy number variant)
CDKN2A Alteration (any significant short variant or structural variant or copy number variant)
SMAD4 Alteration (any significant short variant or structural variant or copy number variant)
MYC Amplified (any significant amplification)
ATM Alteration (any significant short variant or structural variant or copy number variant)
BRCA1 Alteration (any significant short variant or structural variant or copy number variant)
BRCA2 Alteration (any significant short variant or structural variant or copy number variant)
PALB2 Alteration (any significant short variant or structural variant or copy number variant)
CHEK2 Alteration (any significant short variant or structural variant or copy number variant)
ERBB2 Amplified (any significant amplification)
GATA6 Amplified (any significant amplification)
MTAP Alteration (any significant short variant or structural variant or copy number variant)
APC Alteration (any significant short variant or structural variant or copy number variant)
RNF43 Alteration (any significant short variant or structural variant or copy number variant)
GNAS Alteration (any significant short variant or structural variant or copy number variant)
STK11 Alteration (any significant short variant or structural variant or copy number variant)
PIK3CA Mutation (any significant short variant)
RB1 Alteration (any significant short variant or structural variant or copy number variant)
KRAS Amplified (any significant amplification)
BRAF Mutation (any significant variant within Exon 11 or Exon 14)
CCNE1 Amplified (any significant amplification)
AKT2 Amplified (any significant amplification)
PTEN Alteration (any significant short variant or structural variant or copy number variant)
ARIDIA Alteration (any significant short variant or structural variant or copy number variant)
SMARCA4 Alteration (any significant short variant or structural variant or copy number variant)
CDK6 Amplified (any significant amplification)
FGFR1 Amplified (any significant amplification)
ARID2 Alteration (any significant short variant or structural variant or copy number variant)
ZNF703 Amplified (any significant amplification)

Pathway-level clusters of genomic features in some examples can include:

TP53/MDM2: TP53 Alteration|MDM2 Amplified
NOTCH/SPEN: NOTCH1 Alteration|NOTCH2 Alteration|SPEN Alteration
BRCA1/2: BRCA1 Alteration|BRCA2 Alteration
CHEK1/2: CHEK1 Alteration|CHEK2 Alteration
FANC: FANCA Alteration|FANCC Alteration|FANCD2 Alteration|FANCE Alteration|FANCE Alteration|FANCG Alteration|FANCL Alteration|FANCM Alteration
AKT1/2/3: AKT1 Mutation|AKT2 Mutation|AKT3 Mutation|AKT1 Amplified|AKT2 Amplified|AKT3 Amplified
CCND1/2/3: CCND1 Amplified|CCND2 Amplified|CCND3 Amplified
CDK4/6: CDK4 Amplified|CDK6 Amplified
HER2: HER2 Amplified|HER2 Mutation
EGFR: EGFR Amplified|EGFR Mutation|EGFR Fusion
ARID1A/SWI/SNF: SMARCA2 Alteration|SMARCA4 Alteration|SMARCB1 Alteration|ARIDIA Alteration|ARID1B Alteration|ARID2 Alteration|PBRM1 Alteration
FGFR/FRS2: FRS2 Amplified|FGFR1 Amplified|FGFR2 Amplified|FGFR3 Amplified|FGFR4 Amplified|FGFR1 Mutation|FGFR2 Mutation|FGFR3 Mutation|FGFR4 Mutation|FGFR1 Fusion|FGFR2 Fusion|FGFR3 Fusion|FGFR4 Fusion
VEGFA/KDR/FLT: FLT1 Mutation|FLT4 Amplified|FLT4 Mutation|KDR Amplified|KDR Mutation|VEGFA Amplified|TFE3 Fusion|KDM5A Mutation|KDM5A Amplified
ALK/ROS1/NTRK: ALK Fusion|ROS1 Fusion|NTRK1 Fusion|NTRK2 Fusion|NTRK3 Fusion
HRAS/NRAS/KRAS amp: KRAS Amplified|HRAS Amplified|NRAS Amplified Additionally, network-level clusters of genomic features can include:

REG Network Alteration: TP53/MDM2, NOTCH/SPEN|SMAD4 Alteration|MYC Amplified|GATA6 Amplified|ATRX Alteration|MTAP Alteration|RBM10 Alteration|SETD2 Alteration|IDH1 Mutation
CDK Network Alteration: CDK4/6|CCND1/2/3, CDKN2A Alteration|RB1 Alteration
DDR Network Alteration: BRCA1/2, FANC|CHEK1/2|PALB2 Alteration|ATM Alteration|ATR Alteration|RAD50 Alteration|RAD51 Alteration|RAD51B Alteration|RAD51C Alteration|RAD51D Alteration|RAD54L Alteration|NBN Alteration|MRE11 Alteration|BRIP1 Alteration|BARD1 Alteration|BAP1 Alteration
PI3K Network Alteration: AKT1/2/3|PIK3CA Mutation|PIK3CA Amplified|PIK3CB Mutation|PIK3CB Amplified|PIK3C2B Mutation|PIK3C2B Amplified|PIK3C2G Mutation|PIK3C2G Amplified|PIK3CG Mutation|PIK3CG Amplified|PIK3R1 Alteration|PIK3R2 Alteration|PTEN Alteration|STK11 Alteration|MTOR Mutation|MTOR Amplified|RPTOR Amplified|RICTOR Amplified|TSC1/2 Alteration|CCNE1 Amplified|FBXW7 Alteration|ZNF703 Amplified
IMM Network Alteration: ARID1A/SWI/SNF|MSI High|TMB High|POLE Alteration|POLD1 Alteration|MLH1 Alteration|MSH2 Alteration|MSH3 Alteration|MSH6 Alteration|PMS2 Alteration|MUTYH Alteration|JAK3 Mutation|PDCDILG2 Amplified
WNT Network Alteration: APC Alteration|CTNNB1 Fusion|CTNNB1 Mutation|GNAS Alteration|RNF43 Alteration
TKI Network Alteration: FGFR/FRS2|VEGFA/KDR/FLT|ALK/ROS1/NTRK|AXL Amplified|AXL Mutation|MET Amplified|MET Mutation|ABL1 Mutation|ABL1 Fusion|ABL2 Mutation|ABL2

Figure 4:
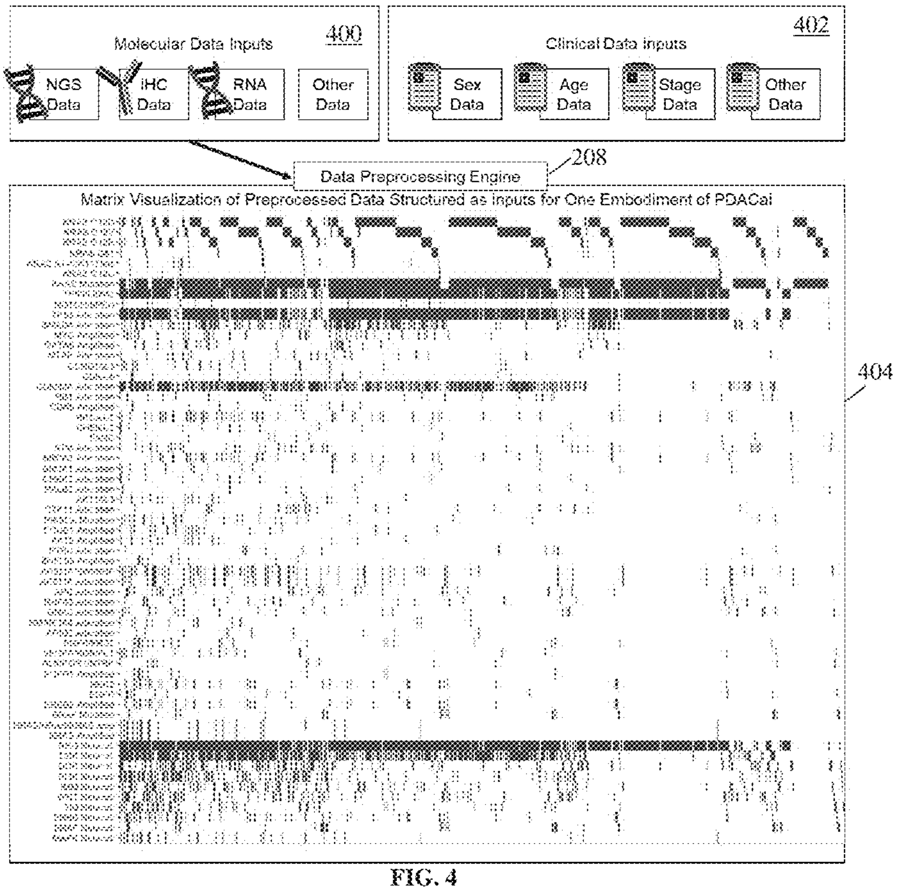
FIG. 4 is a heatmap of model input data including next generation sequencing (NGS) data represented as molecular data.

Fusion|PDGFRA Amplified|PDGFRA Mutation|PDGFRB Amplified|PDGFRB Mutation|KIT Mutation|KIT Amplified|KIT Fusion|RET Mutation|RET Amplified|RET Fusion ERBB Network Alteration: EGFR|HER2|NRG1 Fusion|NRG1 Amplified|PTPN11 Mutation ERBB3 Mutation|ERBB3 Amplified BRAF Network Alteration: BRAF Amplified|BRAF Mutation|BRAF Fusion|ARAF Fusion|RAFI Fusion MAPK Network Alteration: HRAS/NRAS/KRAS amp|HRAS Mutation|NRAS Mutation Referring to FIG. 4, a heatmap of model input data including NGS data represented as molecular data is illustrated. In this example, the therapy prediction device 102 preprocesses the molecular data and/or the clinical data of the input or obtained training and validation data to generate final model input data. In some examples, portions of the training and validation data include unstructured data (e.g., results reported by commercial laboratories and/or clinical features from patient medical history). In these examples, the therapy prediction device 102 can convert the extracted raw data to a standardized nomenclature aligned to input definitions, which can be lab-agnostic for CLIA NGS panels with adequate coverage of raw inputs, for example.

In one example, the standardized nomenclature can be assay type+analyte+result+interpretation, although other standardized nomenclatures can be used. In this example, the assay types can include NGS short variant, NGS copy variant, NGS structural variant, protein expression by IHC, predictions generated by bonus models trained on patient subsets with coverage for optional features (e.g., available PD-L1/HER2 expression), individual values imputed stochastically for patients when optional data is considered missing (e.g., test not performed), protein expression by RPPA, phosphoprotein expression by RPPA, protein expression by GC-MS/LC-MS, and/or RNA expression by NGS, for example. The analyte in the standardized nomenclature can be a Human Genome Organization (HUGO) gene symbols or recognized aliases and the result can be descriptive results or recognized aliases, quantitative/semi-quantitative results, and/or thresholding based on standard pathology guidelines for HER2 IHC.

In some examples, raw input data (binarized to 0/1) is derived from extracted data based on the above-identified definitions. Using those definitions, gene-level input features are advantageously expanded to variant-level features and/or reduced to pathway-level features. Additionally, features with zero variance (i.e., all 0s or all 1s) are not useful for training and can be omitted from the final model input data. Further, the final model input data can be extended to new features beyond those identified above at the pathway-level, gene-level, and/or variant-level with supporting evidence of biological significance and technological improvements of the assay.

Referring back to FIG. 3, in step 302, the therapy prediction device 102 separates patients associated with the final model input data into training and validation cohorts for each of the therapy options. More specifically, the therapy prediction device 102 defines the overall training cohort as well as sets aside an independent validation cohort for each therapy option. In some examples, algorithms that minimize potential bias of potential and/or known confounders can be used to ensure balanced representation of important features.

For example, the initial_split function from the rsample package implemented in an R/Programming environment can be used to assign patients who received FFX to either the FFX training cohort or the FFX validation cohort: rsample::initial_split(data, strata, prop=0.6, pool=0.1), wherein the data is the machine learning input feature matrix representation of features (rows) and patients (columns) (or vice versa) explained above with reference to step 300, the strata is a feature or composite feature that should remain balanced after splitting individuals into the training cohort and the validation cohort, the prop is a 60/40 split in some examples (i.e., the proportion of data to be retained for modeling/analysis), although other splits can be used, and the pool is a 10% threshold for pooling features (i.e., a proportion of data used to determine if a particular group is too small and should be pooled into another group), although other percentages can also be used.

In one example of the strata, a cohort-specific summary of a single composite feature (DDR_SEX_AGE) chosen as the strata to be balanced can be derived from the concatenation of DDR Network Status, Sex at Birth, and Binarized Age at Diagnosis>=63 years, as illustrated below:

| DDR_SEX_AGE (# Individuals Represented by the Composite Feature) | |
|---|---|
| DDRmut_Female_63less | 35 |
| DDRmut_Female_63plus | 23 |
| DDRmut_Male_63less | 43 |
| DDRmut_Male_63plus | 35 |
| DDRwt_Female_63less | 156 |
| DDRwt_Female_63plus | 148 |
| DDRwt_Male_63less | 169 |
| DDRwt_Male_63plus | 160 |

For this example, DDR Network Status was chosen based on correlations between outcomes in patients receiving FFX and similar treatments in PDAC.

Accordingly, the therapy prediction device 102 in this example can specify features that should be represented in balanced proportions across independent cohorts and apply appropriate methods to assign/reassign/stratify patients without any knowledge of the response variable. In other examples in which the goal is to distinguish therapies that share a common backbone, but each includes distinct secondary agents (e.g., "5FU plus Irinotecan" versus "5FU plus Oxaliplatin"), treatment outcomes that align uniquely to one therapy option and not the other therapy option can be annotated prior to allocating patients to the training and validation cohorts. Patients whose treatment outcomes align to both therapy options simultaneously (e.g., FFX aligns to both "5FU plus Irinotecan" and "5FU plus Oxaliplatin" options) may be allocated to the training cohorts for both therapy options. To avoid training bias on these individuals that cause the therapy-specific model predictions to converge, their treatment outcomes can be omitted from a similar fraction of ensemble models designated during the training process for each therapy option.

In step 304, the therapy prediction device 102 samples training and cross-validation subsets from each of the training cohorts generated in step 302. In this example, steps 302-314 are performed for each of the two therapy options (i.e., FFX and GA), although examples of one or more of these steps may be described with reference to one therapy option or the other. In this example, a subset refers to the patients and/or features selected as inputs for training of a single model of a plurality of models, which may vary based on the sampling methods chosen. In some examples, the consensus modeling engine 214 may assign different weights to the set of models that were trained on final model input data that included an optional feature in contexts where that feature may or may not have a known result, as explained in more detail below, which allows this technology to be better equipped to handle missing data values (e.g., HER2 IHC).

Thus, in this example, the therapy prediction device 102 can randomize patients (+/− stratified balancing for covariates/etc.) to multiple training subgroups that will be used to train individual machine learning models separately for varying subsets of individuals (i.e., bootstraps). The therapy prediction device 102 repeats this for subsets with data available for one or more optional features (in addition to certain specified mandatory features), which will be used to train "bonus" individual machine learning models with an expanded features space. The number of subgroups created may be proportional to the number of individuals with data available for optional features relative to the total number of training subgroups without any optional features.

For example, if 15% of patients in the training cohort have data available for a set of optional features, and 1000 models will be trained without optional features, then 150 "bonus" machine learning models may be trained with optional features. Predictions generated by these 150 models will only apply to contexts in which all patients have data available for the relevant optional features and predictions from the 1000 models without optional features still apply to all contexts.

In step 306, the therapy prediction device 102 trains the MLM 216, or one or more machine learning models that will form part of the MLM 216 (e.g., when the MLM 216 is an ensemble model) to predict treatment response data. In some examples, the MLM 216 is trained based on the final model input data, the subsets sampled in step 304, model training parameters, and treatment response data. Thus, the therapy prediction device 102 can define machine learning parameter ranges, generate randomized parameter values, and assign parameter sets to each subset sampled in step 304. Individual machine learning models can then be trained on varying subsets with pre-defined parameter sets.

In some examples, the model raining parameters are defined by TRAINED_MODEL=mlr::train(mlr::makeLearner(cl="surv.cforest", maxdepth=10, replace=FALSE, fraction=0.6, mtry=3, ntrec=3000), mlr::makeSurvTask (data, target=c("time", "event"))), where the data is obtained by joining relevant data from the machine learning input feature matrix (e.g., the final model input data) for a subset of patients to a matrix of "time" (e.g., numerical in days) and "event" (e.g., event status is assigned to 0 or 1 based on presence or absence of censoring, respectively) data from the treatment response data for the same patients. Thus, in the treatment response data "time" is defined in some examples as days between initiation and discontinuation of a treatment in a given context (e.g. FOLFIRINOX or a similar regimen given in the first line setting for the treatment of advanced PDAC) for patients whose disease progressed in that context. The discontinuation could be considered an uncensored "event" in some examples and is therefore represented by a value of 1 using a random survival forests (RSF) methodology. For patients whose disease has not yet progressed in the relevant context, "time" can be defined as days between initiation and the last dose of a treatment that was administered, and the censored "event" can be represented by a value of 0 in this example.

Based on the machine learning methodology implemented, varying sets of parameters can be used when each model is trained (e.g., by sampling random numbers given a range or distribution). In one embodiment, the RSF algorithm allows users to set the "maxdepth" for the maximum tree depth. Restricting tree depth reduces the complexity of each trained model and it may be advantageous to integrate predictions from both more and less complex models into the MLM 216 depending on the properties of the input data and the relative importance of individual features and the relationships between features.

Accordingly, in some examples, a random survival forests (RSF) method can be implemented in step 306 in an R programming environment. With RSF, ensemble models are trained on varying subsets of either the FFX training cohort or the GA training cohort generated in step 304 and cross-validated using treatment-specific response data in the form of PFS outcomes. The format of the treatment-specific response data used by RSF can include a PFS duration in days (e.g., interval time on therapy without disease progression) and a binary event-based outcome status of "1" representing when a progression event had occurred or "0" representing when a progression event has not yet occurred and this duration may be considered a right-censored event. This format of treatment-specific response data is also used when evaluating statistical differences in PFS using Cox regression or ordinal Cox regression (which can be used to assess the predictive performance of the MLM 216 in distinguishing upper versus middle versus lower tertiles for the independent FFX validation cohort and the independent GA validation cohort, as explained in more detail below).

In step 308, the therapy prediction device 102 optionally generates single model performance metrics for each individual machine learning model generated in an iteration of steps 304-306. After the training and cross-validation of step 306 have been completed to create one or more trained models, the model outputs for each individual single model can be independently generated based on input data (e.g., derived from the machine learning input feature matrix and/or final model input data) from one or more patients. In some examples, the following algorithm implemented in an R programming environment using the pec package can be used to generate the model outputs:

pec::predictSurvProb(object, newdata, times), wherein the object is a single trained model, the newdata is derived from the machine learning input feature matrix for the relevant patients, and the times is a sequence of times in days for which probabilities should be predicted by the RSF method.

In one example of the MLM 216, the following sequence can be used to represent an approximate range of 4 to 14 months in 1 month (i.e., 30 days) increments: 120, 150, 180, 210, 240, 270, 300, 330, 360, 390, 420 days. This range was chosen based on the distribution of treatment response data for the FFX training cohort generated in step 302. The same range was chosen based on a similar distribution of treatment response data for the GA training cohort. Computation time is increased if a longer range of time is desired or if the range is split into shorter increments.

The raw model outputs from the pec::predictSurvProb function represent survival probabilities ("probability_of_event") with a column for each "time_point" represented in "times" and a row for each patient represented in "newdata." In one example, the raw model outputs from each trained model based on the FFX training cohort can be transformed into a single numerical value representing the predicted median PFS outcome (defined as "time_interpolated_median_risk" below) for each patient represented in "newdata" using the following linear interpolation algorithm implemented in an R programming environment:

"risk_value"="probability_of_event"

time_right_of_median_risk=the first "time_point" with a "risk_value">=0.5 (if available, otherwise 120 in this example, which is the earliest time point in "times")

time_left_of_median_risk=the last "time_point" with a "risk_value"<0.5 (if available, otherwise 420 in this example, which is the latest time point in "times")

risk_right_of_median_risk=the "risk_value" at "time_right_of_median_risk"

risk_left_of_median_risk=the "risk_value" at "time_left_of_median_risk"

risk_slope_near_median=(0.5−"risk_left_of_median_risk") divided by ("risk_right_of_median_risk"−"risk_left_of_median_risk"))

time_interpolated_median_risk="time_left_of_median_risk"+("risk_slope_near_median" divided by ("time_right_of_median_risk"−"time_left_of_median_risk"))

The output time_interpolated_median_risk is calculated independently for each patient in this example. After training has been completed, the therapy prediction device 102 can compute and save a copy of the raw model outputs as well as the time_interpolated_median_risk values for all patients. In some examples, these values are utilized by the consensus modeling engine 214 as a reference population cohort when normalizing predictions generated for patients.

With the trained model outputs, the therapy prediction device 102 optionally determines single model performance metrics for the trained models. Performance metrics for the trained models can include sensitivity, specificity, false positive rate, false negative rate, true positive rate, true negative rate, accuracy, Matthew's correlation coefficient, c-index, among others. In one example, a single model's performance after the completion of training for a given model based on a given training subset is not taken into account by the consensus modeling engine 214. In some embodiments, the variables of importance (i.e., quantitative values assigned to features that reflect their contributions to a model's performance) calculated from individually trained models may provide insights into the inner workings of each model; however, the performance of individual models or the importance of individual features are not required inputs into the consensus modeling engine.

In step 310, the therapy prediction device 102 combines model outputs from multiple of the trained models based on input data (i.e., required machine learning input feature matrix and/or the final model input data) from one or more patients. In one example, a single model output value representing the predicted median progression-free survival in days is generated from a single trained model as described above. After creating 200 individually trained models from 200 training subsets sampled in step 304 from the FFX training cohort generated in step 302, for example, a total of 200 predictions can be generated for any number of patients with data aligned to the required machine learning input feature matrix. Since each model was trained on various samplings of training subsets, the distribution of predicted model outputs may be skewed from one trained model when compared to another trained model for the same group of patients. By saving a copy of the model outputs from the broader FFX training cohort, the consensus modeling engine 214 can convert the quantitative model output in days into a ranked percentile relative to a reference population.

In one example, the entire FFX training cohort is included in the reference population for all predictions related to FFX response, and the entire GA training cohort is included in the reference population for all predictions related to GA response. However, in another example, predictions from the trained models are generated and saved for the entire FFX validation cohort and consensus model outputs are normalized to a self-contained reference population represented by the FFX validation cohort. In yet another example, predictions from trained models are generated and saved for a superset of the FFX training cohort, the FFX validation cohort, and additional cohorts (e.g., batches of new patients with relevant data added on a quarterly or yearly basis) where consensus model outputs can be normalized to a broader reference population that is more representative of the broader patient population.

In other examples, the consensus modeling engine 214 is generalizable to any set of trained models where multiple variations of one or more machine learning model training algorithms can be implemented. In these examples, the raw model outputs may differ from examples that utilized RSF with specific model training parameters. Instead of converting a time series of event probabilities for each individual patient into a time_interpolated_median_risk, one or more specific time-dependent probabilities (e.g., probability of an event at time=200 days) can be utilized as the basis for the model outputs. For a given patient, the transformation of this numerical value generated by each trained model into a relative ranking normalized to each reference population can be implemented for multiple distinct methods with distinct model training parameters and for distinct feature selections.

Additionally, the consensus modeling engine 214 can combines all relevant predictions based on model outputs generated for an individual patient after normalization to the reference population representing each trained model. In some examples, the reference population is uniformly defined as the FFX training cohort for predictions related to FFX response and the GA training cohort for predictions related to GA response. In other examples in which NGS input data are features for all trained models and IHC input data are features for some but not all trained models, the consensus modeling engine 214 can only include patients in a reference population if they have adequate coverage of the required input features that are relevant to that set of trained models.

In step 312, the therapy prediction device 102 optionally generates consensus model performance metrics for the consensus model, which is also referred to herein as MLM 216. In some examples, the treatment response data is not required to generate consensus model outputs, but is used to evaluate the performance of the consensus model outputs. The consensus model performance metrics can be generated as explained above in step 308 with reference to the single model performance metrics.

Figure 5:
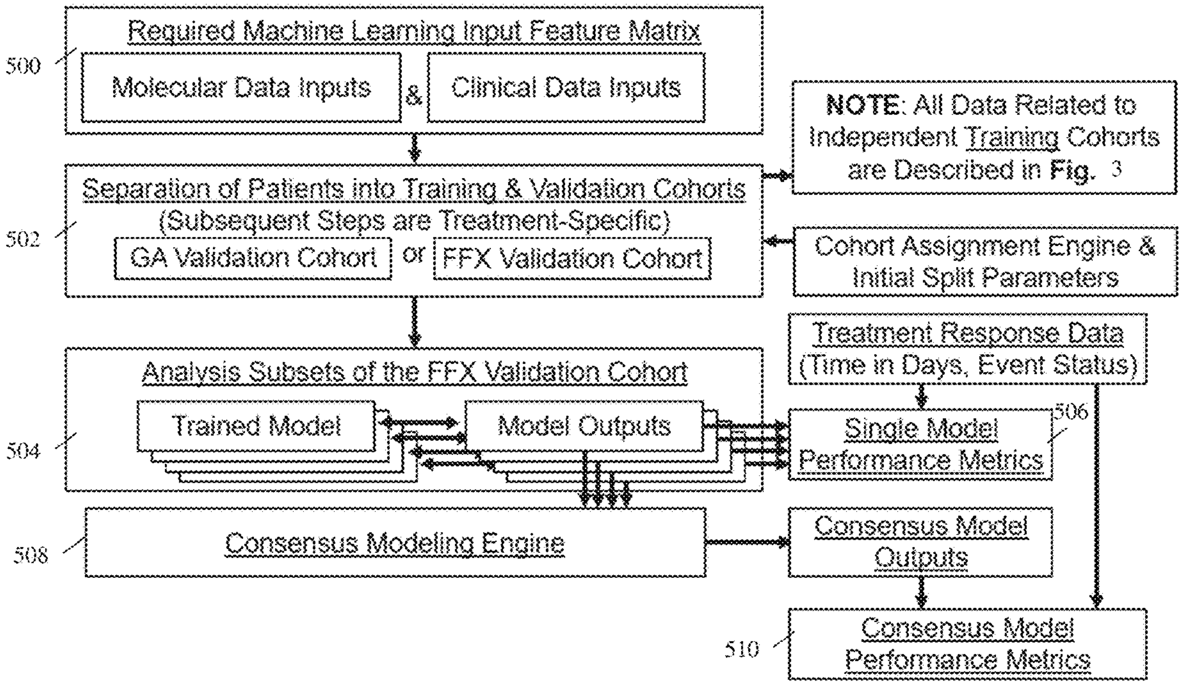
FIG. 5 is a flowchart of an exemplary method for validating treatment-specific models.

Referring now to FIG. 5, a flowchart of an exemplary method for validating treatment-specific models is illustrated. In step 500, the therapy prediction device 102 obtains training and validation data, including molecular data and clinical data for a plurality of patients, as explained above with reference to step 300 of FIG. 3.

In step 502, the therapy prediction device 102 separates patients into training and validation cohorts, also as explained above with reference to step 302 of FIG. 3. Whereas the training described and illustrated with reference to FIG. 3 utilizes the training cohorts, the validation cohorts generated in step 302 or 502 is used by the therapy prediction device 102 to validate the MLM 216.

In some examples, patients with PFS outcome data are filtered to include therapies that were given in the 1st line of therapy setting for advanced or metastatic disease (where outcomes are generally more comparable between groups of patients). Each 1st line treatment with PFS outcome data with a minimum documented duration of 30 days (censored or uncensored) can be aligned to one or more therapy option(s) based on the specific agents that the patient received. Since the goal of the MLM 216 is to distinguish relatively inferior or superior responses to one therapy (e.g., FFX) from relatively inferior or superior responses to another therapy (e.g., GA), the therapy prediction device 102 can exclude treatment outcomes that include agents aligning to both FFX and GA therapy options from the training and validation cohorts.

The ensembles of RSF models for FFX can be trained and validated specifically on 1st line treatment outcomes that align to all three agents defined above for FFX (where alternative agents of the same class were considered acceptable) and aligned to neither of the two agents defined above for GA. Additionally, the ensembles of RSF models for GA can be trained and validated specifically on 1st line treatment outcomes that align to both agents defined above for GA (where alternative agents of the same class were considered acceptable) and aligned to none of the three agents defined above for FFX. Other methods for generating the validation cohorts can also be used in other examples. Additionally, although explained with reference to FFX or GA, steps 504-510 are performed in this example for each of a plurality of treatments reflected in the training and validation input data.

In step 504, the therapy prediction device 102 analyzes the subsets of the validation cohort to determine whether the MLM 216 is validated (e.g., exceeds an accuracy threshold). The predicted model output values generated by the MLM 216 can be represented as percentiles within each of the four cohorts: FFX training cohort, GA training cohort, FFX validation cohort, and GA validation cohort. For the purposes of validation, the percentile values from predicted model outputs can be placed into one of three categories for each therapy option, separately within each cohort: upper tertile (therapy-specific percentile between 66.7% and 100.0%), middle tertile (therapy-specific percentile between 33.4% and 66.6%), and lower tertile (therapy-specific percentile between 0.0% and 33.3%). Other types or number of categories or buckets can also be used in other examples of this technology.

Accordingly, in some examples, an ensemble modeling approach can be used by the therapy prediction device 102 to generate therapy-specific predictions. In one particular example, a total of 50 ensemble models intended to predict FFX-specific outcomes were trained and cross-validated (e.g., as explained with reference to step 306 of FIG. 3) on varying subsets of treatment data from the FFX training cohort. A total of 50 ensemble models intended to predict GA-specific outcomes were also trained and cross-validated (e.g., as explained with reference to step 306 of FIG. 3) on varying subsets of treatment data from the GA training cohort.

Raw model prediction output values can then be generated for all patients using the 50 FFX-specific ensemble models and the 50 GA-specific ensemble models. Separately for each of the 100 ensemble models in total, raw model prediction output values can be sorted and ranked within each cohort to compute a raw percentile value. Raw percentile values generated by the 50 relevant therapy-specific ensemble models for each cohort can then be averaged to generate a single value used to sort and rank predictions into the final percentiles used to define upper tertile versus middle tertile versus lower tertile. These therapy-specific group assignments can then be used to assess the statistical significance of differences in PFS between the three tertiles using ordinal Cox regression in the independent FFX VALIDATION COHORT and the independent GA validation cohort. In some examples, steps 506-510 can be performed by the therapy prediction device 102 in the same manner as explained above with reference to steps 308-312 of FIG. 3, respectively.

Figure 6A:
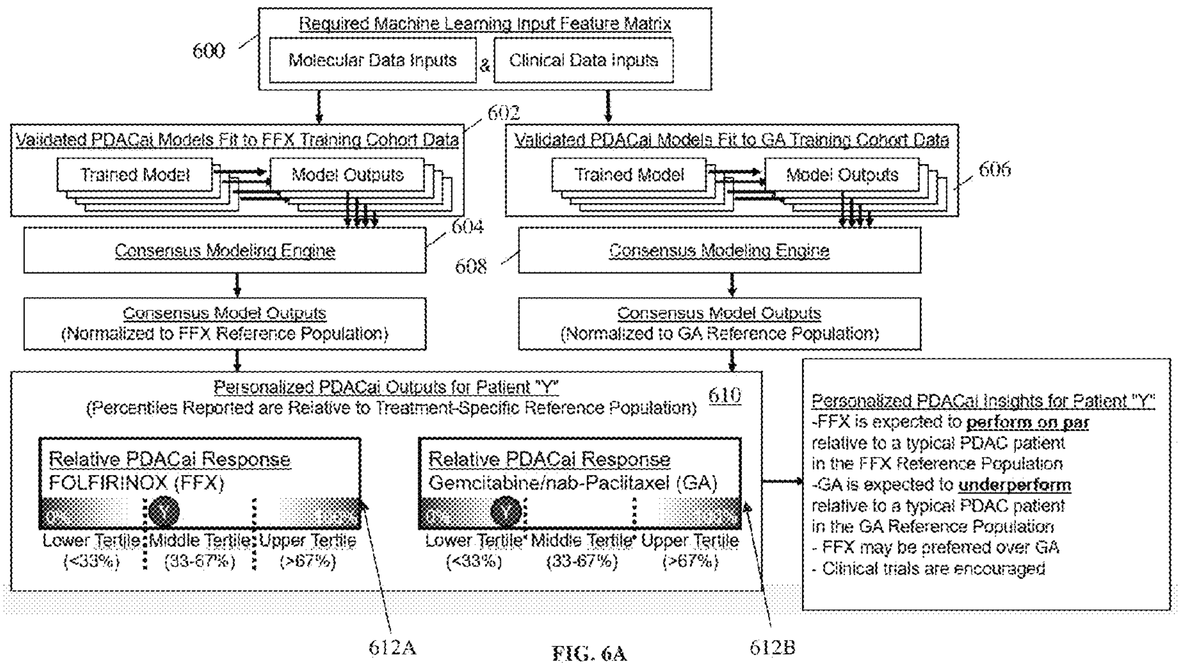
FIGS. 6A-B are flowcharts of an exemplary method for applying trained and validated treatment-specific models to generate consensus model predictions.
Figure 6B:
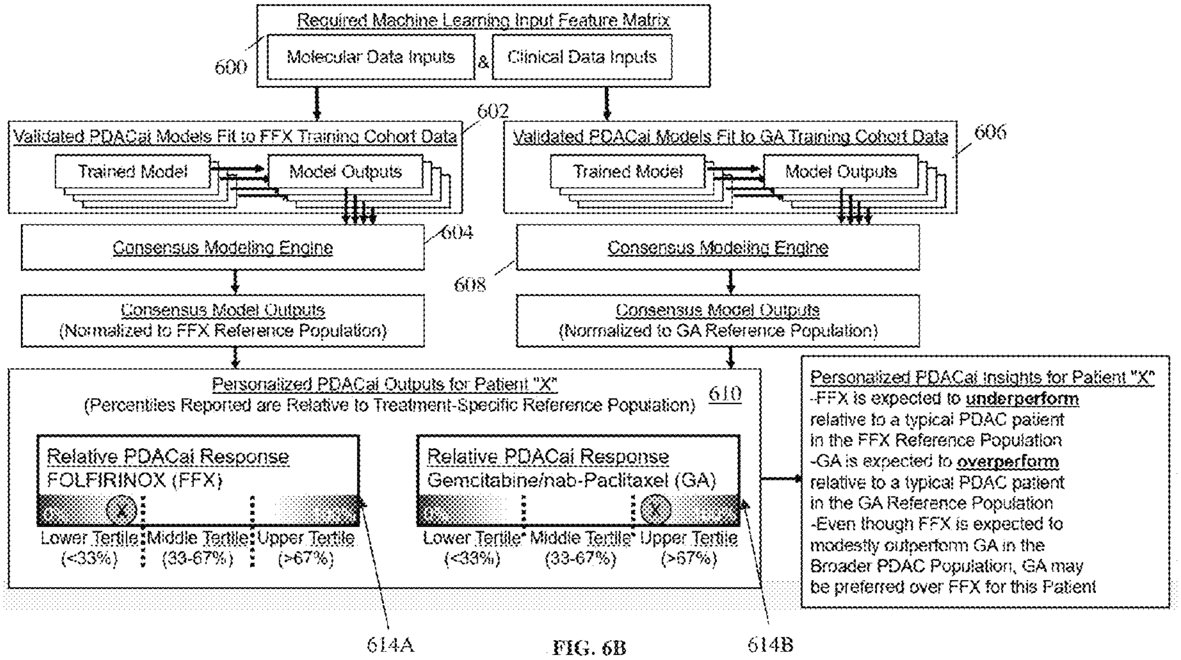

Referring to FIG. 6A-B, flowcharts of an exemplary method for applying trained and validated treatment-specific models to generate consensus model predictions are illustrated. Referring more specifically to FIG. 6A, in step 600 the therapy prediction device 102 obtains patient input data for a particular patient, which includes molecular data and clinical data in this example. The molecular and clinical data can be for the same or a subset of the features represented in the molecular and clinical data of the training and validation data obtained in step 300, for example. The patient input data can be obtained form one of the client devices 106(1)-106(*a*), for example.

In step 602, the therapy prediction device 102 applies the MLM 216 to the patient input data. In this example, a subset of the models that collectively comprise the MLM 216 are applied to the patient input data, with the subset corresponding to validated models fit to the FFX training cohort data.

In step 604, the consensus modeling engine 214 of the therapy prediction device 102 combines model outputs from the validated models applied to the patient input data in step 602 to generate consensus model outputs normalized to an FFX reference population.

In step 606, the therapy prediction device 102 again applies the MLM 216 to the patient input data. In this example, a subset of the models that collectively comprise the MLM 216 are applied to the patient input data, with the subset corresponding to validated models fit to the GA training cohort data.

In step 608, the consensus modeling engine 214 of the therapy prediction device 102 combines model outputs from the validated models applied to the patient input data in step 606 to generate consensus model outputs normalized to an GA reference population.

In step 610, the therapy prediction device 102 generates a personalized therapy response prediction for the patient associated with the patient input data obtained in step 600. The personalized therapy response prediction can be provided via a GUI or other interface to the one of the client devices 106(1)-106(*a*) from which the patient input data was obtained in step 600. In some examples, the GUI can include graphical representations 612A-B that illustrate a tertile in which the patient falls based on the output of the MLM 216 for the FFX and GA response, respectively.

The exemplary graphical representations 612A-B of FIG. 6A indicate that the patient is expected to perform on par relative to a typical patient in the FFX reference population and GA is expected to underperform relative to a typical patient in the GA reference population. Thus, FFX may be a preferred frontline treatment over GA although since the FFX response output from the MLM 216 did not place in the upper tertile, clinical trials may also be encouraged for this patient.

Referring more specifically to FIG. 6B, the therapy prediction device 102 can perform steps 600-610 as explained above, but for a different patient having different associated patient input data obtained in step 600. Thus, in step 610 in this example the therapy prediction device 102 generates different personalized therapy response predictions including graphical representations 614A-B that illustrate a tertile in which the patient falls based on the output of the MLM 216 for the FFX and GA response, respectively.

The exemplary graphical representations 614A-B in this example indicate that the patient is expected to underperform relative to a typical patient in the FFX reference population and GA is expected to overperform relative to a typical patient in the GA reference population. Thus, even though FFX is expected to modestly outperform GA in the broader population, the technology described and illustrated herein yields GA as the preferred and recommended frontline therapy over FFX for this patient.

Accordingly, applying the technology described herein to make personalized predictions for a new patient (i.e., an individual not included in the original training and/or validation cohorts) includes two of the following (one for each therapy option):

- Upper FFX prediction: this patient has similar model predictions to those categorized as having increased benefit from FFX (or objectively superior responses to FFX) based on comparisons to the FFX reference population.
- Middle FFX prediction: this patient has similar model predictions to those categorized as having typical benefit from FFX (or average responses to FFX) based on comparisons to the FFX reference population.
- Lower FFX prediction: this patient has similar model predictions to those categorized as having decreased benefit from FFX (or objectively inferior responses to FFX) based on comparisons to the FFX reference population.
- Upper GA prediction: this patient has similar model predictions to those categorized as having increased benefit from GA (or objectively superior responses to GA) based on comparisons to the GA reference population.
- Middle GA prediction: this patient has similar model predictions to those categorized as having typical benefit from GA (or average responses to GA) based on comparisons to the GA reference population.
- Lower GA prediction: this patient has similar model predictions to those categorized as having decreased benefit from GA (or objectively inferior responses to GA) based on comparisons to the GA reference population.

In some examples, the therapy prediction device 102 calculates whether a patient has personalized therapy response predictions that are categorized as an upper FFX (or GA) prediction versus a middle FFX (or GA) prediction versus a lower FFX (or GA) prediction can depend on pairs of numerical cutoff values (one splitting upper versus middle; the other splitting middle versus lower), which can be defined separately for the FFX reference population and the GA reference population. Each therapy-specific reference population is typically defined as the FFX (or GA) validation cohort as described above.

In examples in which the initial validation study has been completed and additional validation studies are underway, reference populations may be expanded into larger cohorts consisting of the original FFX (and/or GA) training cohort, the original FFX (and/or GA) validation cohort, and/or an extended FFX (and/or GA) cohort, which would be updated on a routine or periodic (e.g. quarterly, yearly) basis with the iterative release of new validation studies that demonstrate improved model performance (e.g., based on C-index, accuracy, sensitivity, and/or specificity).

Figure 7:
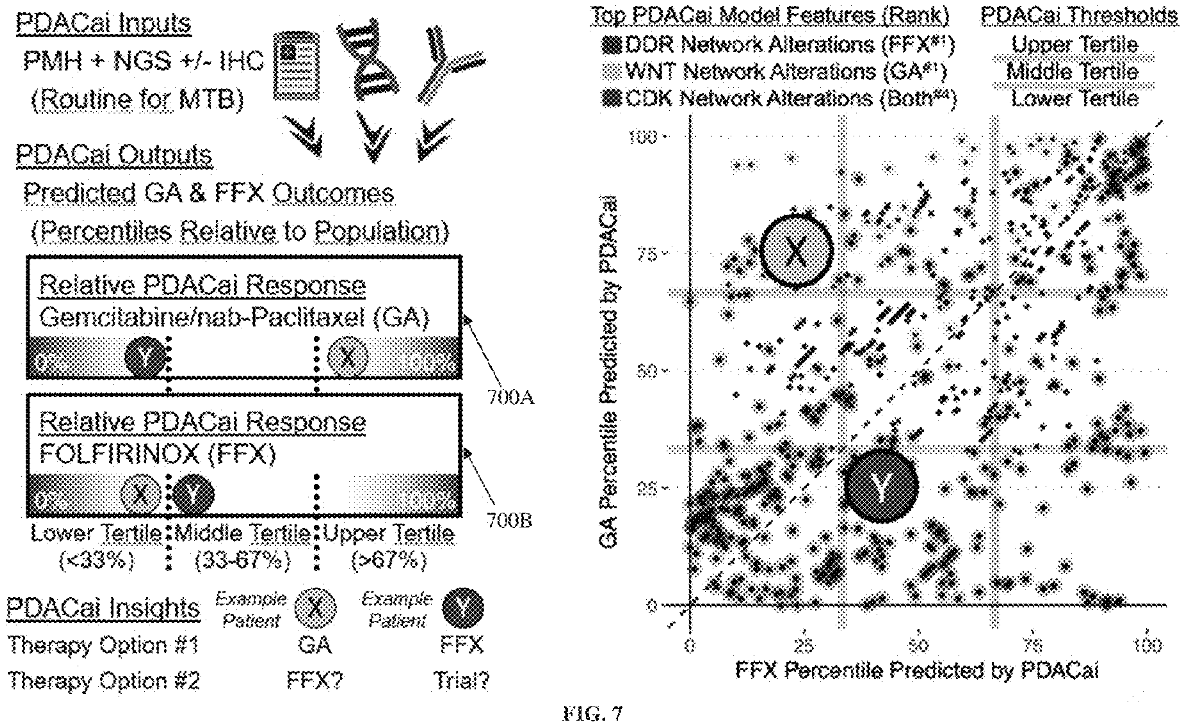
FIG. 7 is an exemplary graphical interface illustrating percentile predictions.

Referring to FIG. 7, an exemplary graphical interface illustrating percentile predictions is illustrated. In this example, the therapy prediction device 102 applies the trained and validated MLM 216 to first and second input data for patient X and patient Y, respectively. The graphical representations 700A-B generated from the personalized therapy response predictions output by the MLM 216 indicate that patient Y falls in the lower GA prediction tertile for GA response but the middle FFX prediction tertile for FFX, which may inform a clinician to recommend a frontline FFX therapy for patient Y over GA. Conversely, patient X falls in the upper GA prediction tertile and the lower FFX prediction tertile providing a relatively strong likelihood that patient X will respond to GA as a frontline treatment as compared to FFX.

Figure 8:
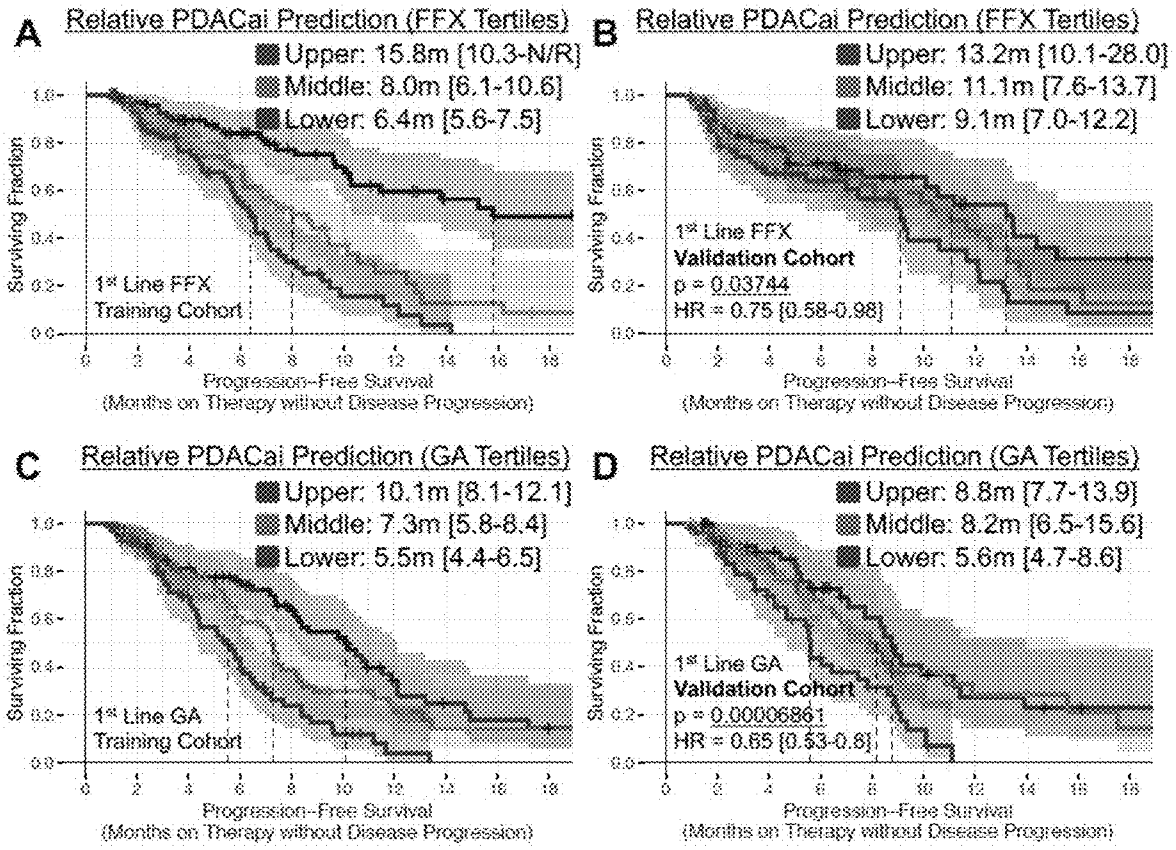
FIG. 8 illustrates Kaplan-Meier (KM) curves of PFS on 1st line therapies from patients allocated to independent training and validation cohorts.

Referring now to FIG. 8, KM curves are disclosed of PFS on 1st line therapies from patients allocated to independent training (A, C) and validation (B, D) cohorts. Actual median PFS [plus 95% CI] in months are summarized in patients assigned to lower, middle, or upper tertiles based on relative predictions. The predictive utility of this technology was confirmed in the independent validation cohorts (B, D) by comparing PFS across tertiles (see p-values and hazard ratios (HR) [plus 95% CI]).

Figure 9:
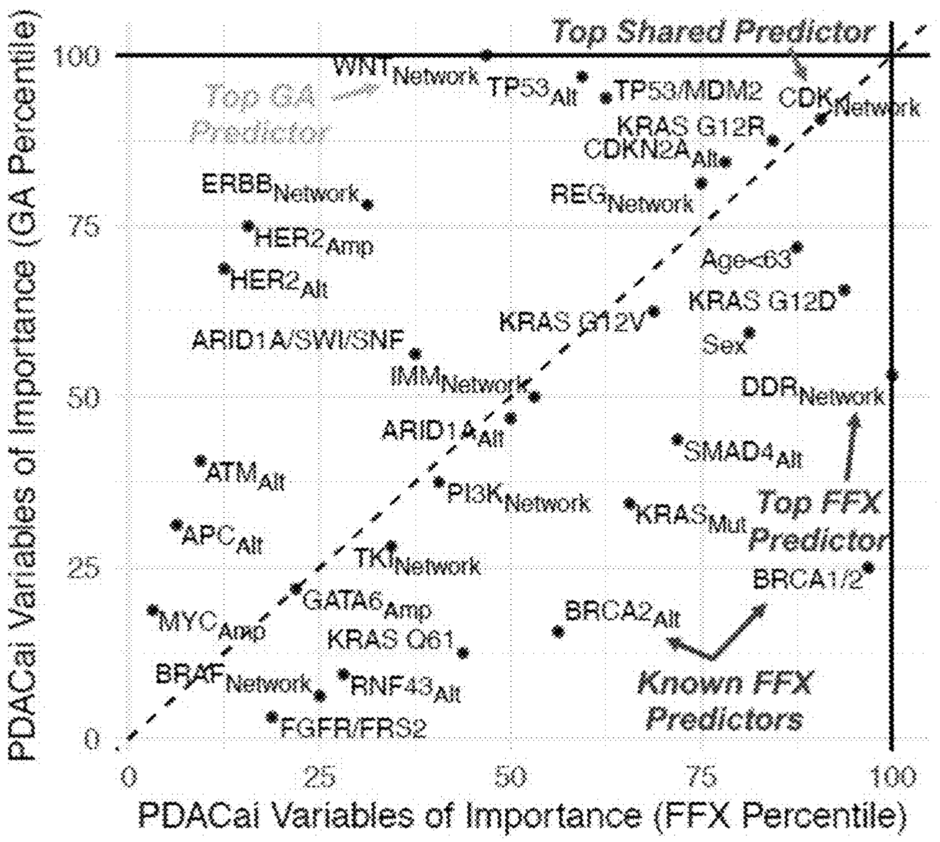
FIG. 9 illustrates relative percentiles of variables of importance calculated from therapy-specific models that utilized a shared set of inputs.

Referring to FIG. 9, relative percentiles are disclosed of variables of importance calculated from therapy-specific models within the MLM 216 that utilized a shared set of inputs including patient sex, age<63 at diagnosis, variant-specific alterations (e.g., KRAS G12D, KRAS G12R, KRAS Q61), gene-level alterations (BRCA2 Alteration), curated pathway clusters (e.g., BRCA1/2), and broader network-level alterations (e.g., DDR Network2). The technology described and illustrated herein helps overcome the limitations of sparse NGS data (in which only a handful of genes are commonly mutated). Median PFS followed predicted trends generated by this technology for each therapy option in the training and validation cohorts.

Figure 10:
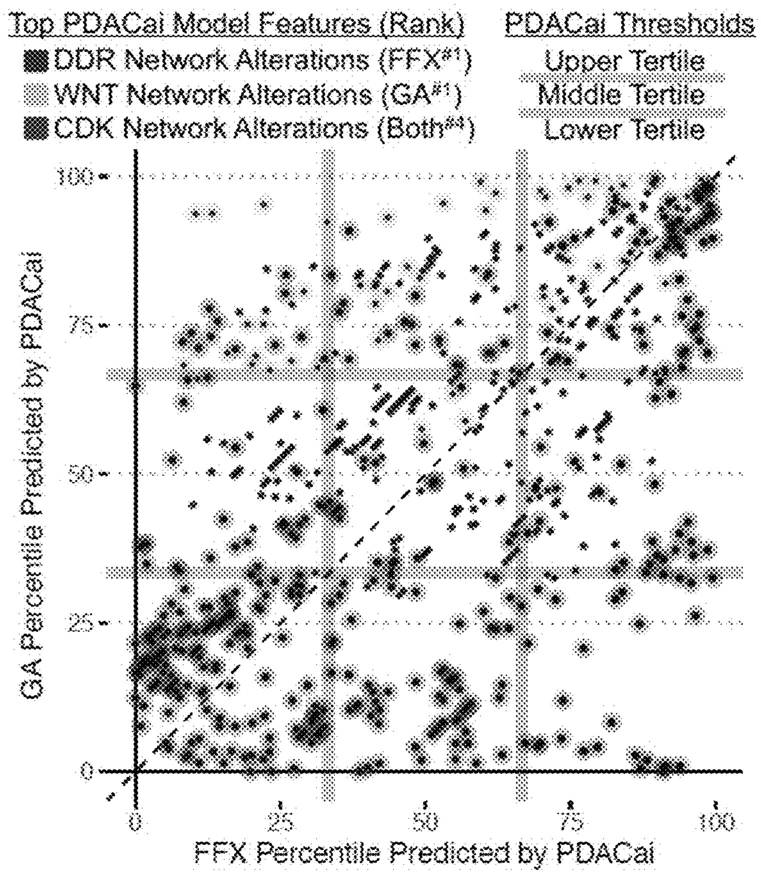
FIG. 10 illustrates a landscape of FFX versus GA percentiles across all cohorts.

Referring to FIG. 10, the landscape of FFX versus GA percentiles across all cohorts highlights how the most important variables for FFX (DDR Network2) and GA (WNT Network) are enriched in a treatment-specific manner respectively for patients with higher values. Top pathway-level features are highlighted for patients with genomic alterations in DDR (BRCA1/2, PALB2, CHEK1/2, ATR/ATM, FANC/MRN, etc2), WNT (RNF43, APC, GNAS, CTNNB1), or CDK (CDKN2A, CDK4/6, CCND1/2/3, RB1) gene networks.

Figure 11:
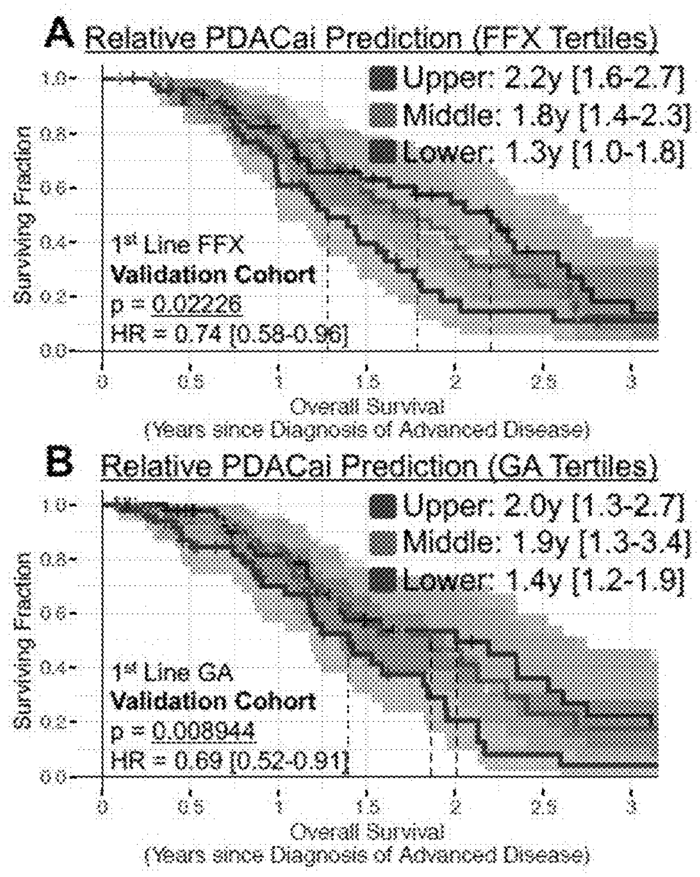
FIG. 11 illustrates KM curves of overall survival in years since advanced diagnosis for treatment specific predictions within independent FFX and GA validation cohorts.
Figure 12:
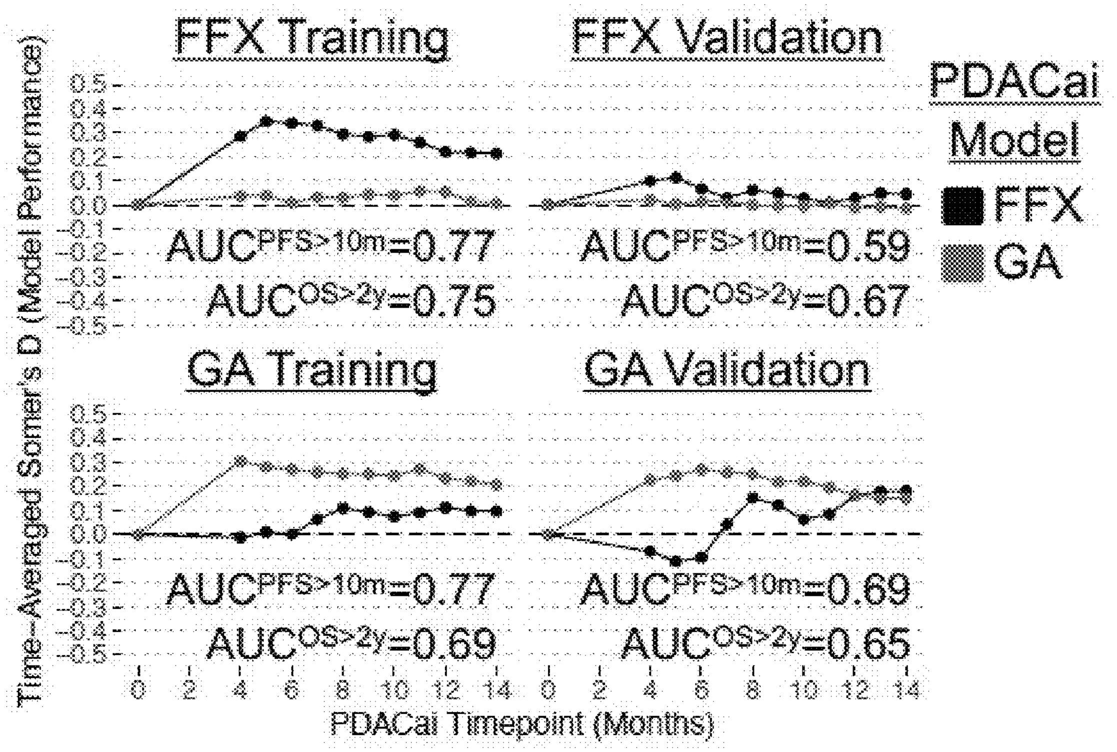
FIG. 12 illustrates time-averaged performance assessed within each cohort comparing PFS against both model predictions.

Referring to FIG. 11, KM curves of overall survival in years since advanced diagnosis for treatment specific predictions within the independent FFX (A) and GA (B) validation cohorts are disclosed. Referring to FIG. 12, time-averaged performance (i.e., higher is better) assessed within each cohort comparing PFS against both predictions by the MLM 216 is illustrated. FFX predictions were generally more predictive of PFS for FFX outcomes than GA outcomes (and vice versa for GA predictions).

Figure 13:
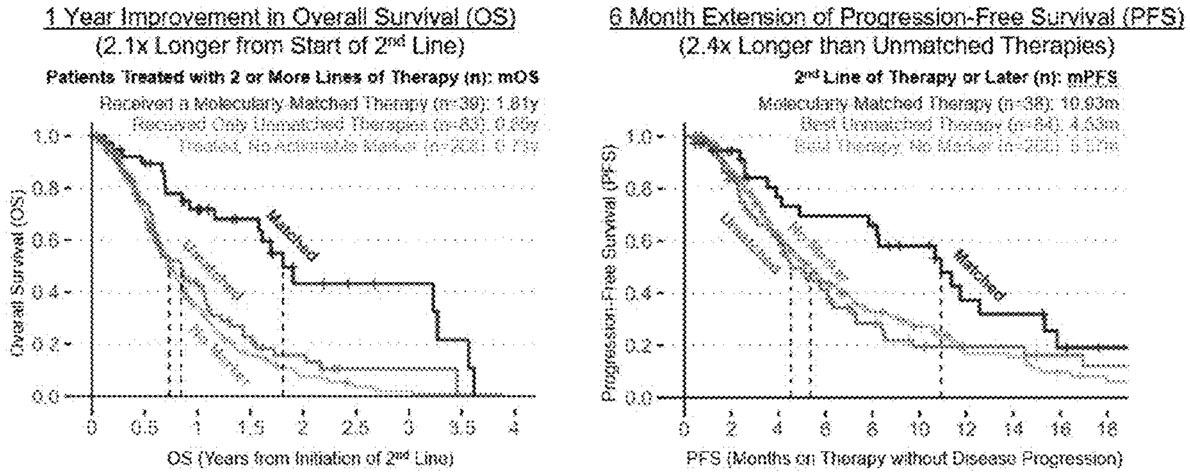
FIG. 13 illustrates OS and PFS improvement for patients treated with matches lines of therapy.

Referring to FIG. 13, OS and PFS improvement for patients treated with matched lines of therapy is illustrated. In this example, the patients that received a matched therapy (i.e., therapy sequencing in accordance with the personalized therapy response predictions output by the MLM 216 as applied by the therapy prediction device 102 to corresponding patient input data) shows significantly longer OS and PFS as compared to patients with unmatched therapies or no actionable marker or prediction. Response to chemotherapy is heterogeneous and difficult to predict in patients with mPDAC. Using this technology, signatures successfully predicted relative differences in PFS for both FFX and GA. This technology advantageously provides for the prospective validation of models that utilize clinical NGS results to deliver insights for treatment sequencing within standard of care and thereby improve patient response and health outcomes.

Interpreting personalized therapy response predictions generated by this technology provide insights into the optimization of treatment decisions for individual patients when taking into account the individual therapy-specific predictions as well as any differences between the therapy-specific predictions. The following examples highlight how this technology could be practically applied to an individual patient with certain predictions using the MLM 216 generated as described and illustrated above.

In one example, an individual oncologist (e.g., medical oncologist) might consider FFX as the preferred 1st line therapy over GA in a patient with an upper FFX prediction and either a middle GA prediction or a lower GA prediction. The absolute difference in individual therapy-specific percentile values may also be informative (FFX Percentile=64; GA Percentile=34) when both therapies fall into the same relative tertile. For therapies that do not have equal benefit regarding PFS outcomes at the equivalent value of a middle tertile, then an adjusted output value that reflects the absolute predicted benefit of each therapy (e.g., expected months of PFS) may be more informative to an oncologist.

In another example, an oncology care team (e.g., multidisciplinary tumor board or molecular tumor board evaluating) may emphasize enrollment into a clinical trial for a patient with both a lower FFX prediction and a lower GA prediction since no standard of care options are expected to be effective for this patient. An alternative interpretation would involve stopping an ongoing standard therapy immediately after early signs of disease progression or unacceptable toxicity have been encountered alongside a lower FFX or GA prediction for that same therapy. The decision to revisit a therapy that was given earlier and is still on the table could be encouraged by an upper FFX or GA prediction for that therapy.

In yet another example, a clinical research organization (e.g., a biopharma company) could use this technology to design clinical trials that account for expected differences in prospectively captured outcomes based on different prediction categories, in particular when therapy-specific models are aligned to the treatment given in the placebo/comparator group (and/or the active treatment group which might include additional novel agents). For trials that evaluate new or existing drug combinations with multiple backbones, this technology could be used to assign which treatment the patients will receive in addition to any new agents being evaluated in combination with the existing agents.

Further, a person or entity (e.g., an insurance company or oncology pathways algorithm embedded in an EMR/EHR system) can use the disclosed technology to pre-authorize or authorize the approval, denial, or prioritization of one or more therapies. For example, FFX can be authorized without additional steps when a physician submits paperwork for a patient with either an upper FFX prediction or a middle FFX prediction or a lower GA prediction).

Having thus described the basic concept of the invention, it will be rather apparent to those skilled in the art that the foregoing detailed disclosure is intended to be presented by way of example only and is not limiting. Various alterations, improvements, and modifications will occur and are intended to those skilled in the art, though not expressly stated herein. These alterations, improvements, and modifications are intended to be suggested hereby, and are within the spirit and scope of the invention.

What is claimed is:

1. A method for improved machine learning modeling for predicting relative benefit of therapy options for a condition, the method comprising:

generating training cohorts and validation cohorts for each of first and second therapy options for a plurality of patients based on training and validation data for the patients obtained via one or more communication networks from one or more data server devices and comprising at least first molecular and clinical data;

generating an ensemble machine learning model, comprising:

sampling training and cross-validation subsets from each of the training cohorts and validation subsets from each of the validation cohorts comprising excluding from the training cohorts and the validation cohorts a set of other patients that received treatment including one or more agents aligned to both the first and second therapy options;

training machine learning models using the training and cross-validation subsets, wherein the machine learning models comprise random survival forest (RSF) models trained to predict treatment response data for each of the first and second therapy options;

validating the machine learning models using treatment-specific response data in the validation subsets to determine that the machine learning models exceed an accuracy threshold, wherein the treatment-specific response data comprises first progression-free survival data; and combining first and second subsets of the machine learning models into the ensemble machine learning model, wherein at least a subset of models in each of the first and second subsets of the machine learning models vary by tree depth and parameter set as a result of the training;

applying the machine learning model to patient data for a patient to generate first and second treatment response data, each corresponding to one of a plurality of categories for each of the first and second therapy options, wherein the patient data is obtained via the communication networks from a client device;

generating, and outputting via the communication networks for display via a display device of the client device, a graphical user interface comprising a representation of the first and second treatment response data with respect to the categories for the first and second therapy options, respectively, to thereby inform treatment of the patient for the condition; and treating the patient in accordance with one of the first or second therapy options as a frontline therapy based on a relative value of the first and second treatment response data, wherein the first and second therapy options comprise Gemcitabine/nab-Paclitaxel (GA) and FOLFIRINOX (FFX) chemotherapeutic agents and the treatment comprises administering chemotherapy to the patient via the GA or FFX chemotherapeutic agents to treat pancreatic adenocarcinoma (PDAC).

2. The method of claim 1, wherein the first molecular and clinical data further comprises, for each of the patients, clusters of genomic features, second progression-free survival data, and an indication of a frontline treatment corresponding to one of the first or second therapy options.

3. The method of claim 1, wherein the first therapy option or second therapy option comprises gemcitabine and nab-paclitaxel, 5-Fluorouracil+nal-Irinotecan+Oxaliplatin, 5-Fluorouracil+Irinotecan+Oxaliplatin, 5-Fluorouracil+

Oxaliplatin, 5-Fluorouracil+Irinotecan, or 5-Fluorouracil+nal-Irinotecan, and the condition comprises pancreatic adenocarcinoma.

4. The method of claim 1, wherein the patient data comprises second molecular and clinical data for the patient and the first and second treatment response data comprises first and second personalized therapy response predictions for the patient with respect to the first and second therapy options, respectively.

5. The method of claim 1, wherein each of the patients is associated with one of two therapy-specific reference populations and the categories correspond to tertiles representing underperformance, expected performance, and overperformance with respect to portions of the therapy-specific reference population corresponding to one of the first or second therapy options, respectively.

* * * * *